United States Patent [19]

Hosono et al.

[11] Patent Number: 5,677,300
[45] Date of Patent: Oct. 14, 1997

[54] PYRIDOTHIAZINEACETIC ACID COMPOUND, PRODUCTION THEREOF AND USE THEREOF

[75] Inventors: Hiroshi Hosono, Ibaraki; Tomoji Aotsuka, Hamura; Yoshiyuki Nakamura, Shizuoka; Tetsuo Matsui, Tsukuba; Hiromichi Ishikawa, Kobe, all of Japan

[73] Assignees: The Green Cross Corporation; Senji Pharmaceutical Co., Ltd., both of Osaka, Japan

[21] Appl. No.: 697,917

[22] Filed: Sep. 3, 1996

Related U.S. Application Data

[62] Division of Ser. No. 343,536, Nov. 29, 1994, abandoned.

[30] Foreign Application Priority Data

Mar. 29, 1993 [JP] Japan .................................. 5-091935

[51] Int. Cl.$^6$ ...................... A61K 31/54; C07D 513/06
[52] U.S. Cl. .................................. 514/224.2; 544/48
[58] Field of Search ............................. 544/48; 514/224.2

[56] References Cited

U.S. PATENT DOCUMENTS

| | | | |
|---|---|---|---|
| 4,784,997 | 11/1988 | Klausener et al. | 224/2 |
| 5,071,849 | 12/1991 | Bozsing et al. | 514/224.2 |

*Primary Examiner*—Johann Richter
*Assistant Examiner*—Laura R. Cross
*Attorney, Agent, or Firm*—Sughrue, Mion, Zinn, Macpeak and Seas

[57] ABSTRACT

A pyridothiazineacetic acid compound of the formula (I)

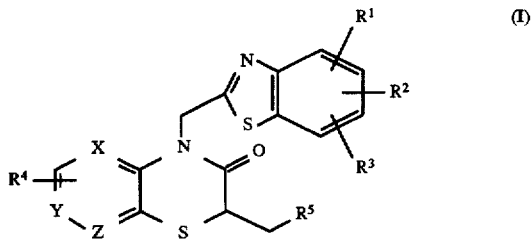

wherein each symbol is as defined in the specification, a pharmaceutically acceptable salt thereof, production thereof, and a pharmaceutical composition, an aldose reductase inhibitor and a preparation for the prevention and treatment of the complications of diabetes, containing the same.

The pyridothiazineacetic acid compound and a pharmaceutically acceptable salt thereof of the present invention have an aldose reductase inhibitory action and are superior in safety. Accordingly, they are useful as a preparation for the prevention and treatment of the complications of diabetes, such as faulty union of corneal injury, cataract, neurosis, retinopathy and nephropathy, particularly, cataract and neurosis. In addition, the production method of the present invention enables efficient production of said pyridothiazineacetic acid compound.

7 Claims, No Drawings

PYRIDOTHIAZINEACETIC ACID COMPOUND, PRODUCTION THEREOF AND USE THEREOF

This is a divisional of application Ser. No. 08/343,536, filed Nov. 29, 1994 now abandoned.

TECHNICAL FIELD

The present invention relates to a novel pyridothiazineacetic acid compound having superior aldose reductase inhibitory activity and a pharmaceutically acceptable salt thereof, production thereof, and pharmaceutical use thereof. The compound of the invention and a pharmaceutically acceptable salt thereof are useful as preparations for the prevention and treatment of the complications of diabetes, such as diabetic cataract, retinopathy, nephropathy and neurosis.

BACKGROUND ART

Traditionally, blood sugar regulators such as insulin and synthetic hypoglycemic agents have been widely used for treating diabetes. Diabetes is a disease which accompanies various complications which are hardly prevented from developing by a mere control of the blood sugar, and a new therapeutic agent for the complications of diabetes has been demanded.

Accumulation of and increase in sorbitol and galactitol in tissues which are caused by chronic hyperglycemia have recently been drawing attention as the mechanism of the onset of the complications of diabetes.

Some literature suggests that a compound having an inhibitory action on the activity of aldose reductase which is an enzyme capable of converting aldose such as glucose or galactose into sorbitol or galactitol, is useful for the treatment of the complications of diabetes, such as cataract, neurosis, nephropathy and retinopathy [see J. H. Kinoshita et al. Biochem. Biophys. Acta, 158, 472 (1968), Richard Poulson et al. Biochem. Pharmacol., 32, 1495 (1983) and D. Dvornik et al, Science, 182, 1145 (1973)].

Based on the foregoing, the study is directed to the prevention and treatment of the complications of diabetes by the inhibition of aldose reductase activity to ultimately inhibit accumulation of polyols such as sorbitol and galactitol.

DISCLOSURE OF THE INVENTION

In view of the above, the present inventors have conducted intensive studies with the aim of developing a preparation for the prevention and treatment of the complications of diabetes, which has an aldose reductase inhibitory action, and found that a certain pyridothiazine compound achieves the object, which resulted in the completion of the invention.

That is, the present invention relates to a pyridothiazineacetic acid compound of the formula (I)

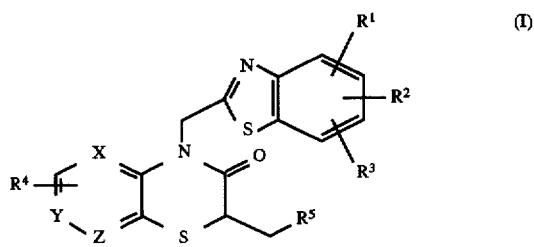

wherein

X, Y and Z are each independent and one of them is a nitrogen atom and the rest are CH, $R^1$, $R^2$ and $R^3$ may be the same or different and each is a hydrogen atom, a lower alkyl or a halogen atom, $R^4$ is a hydrogen atom, a lower alkyl or a halogen atom, and $R^5$ is an optionally esterified carboxyl, and a pharmaceutically acceptable salt thereof.

The present invention also relates to the production of the pyridothiazineacetic acid compound of the aforementioned formula (I) or a pharmaceutically acceptable salt thereof, comprising (a) reacting a compound of the formula (II)

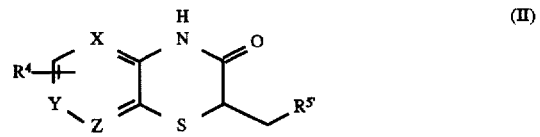

wherein $R^4$, X, Y and Z are as defined above and $R^{5'}$ is an esterified carboxyl, or a salt thereof with a compound of the formula (III)

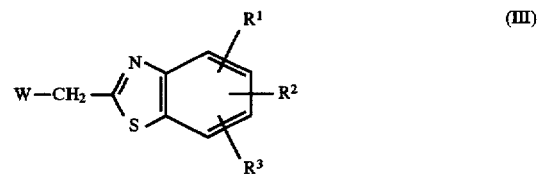

wherein $R^1$, $R^2$ and $R^3$ are as defined above and W is a halogen atom or $-OSO_2R^6$ wherein $R^6$ is a lower alkyl, trifluoromethyl or substituted or unsubstituted phenyl, or (b) reacting a compound of the formula (IV)

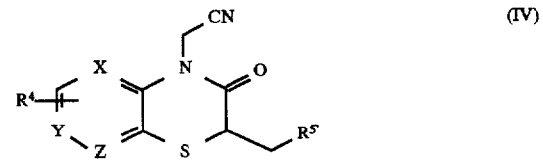

wherein $R^4$, $R^{5'}$, X, Y and Z are as defined above, or an acid addition salt thereof with a compound of the formula (V)

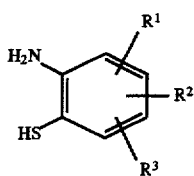 (V)

wherein $R^1$, $R^2$ and $R^3$ are as defined above, or an acid addition salt thereof, followed by hydrolysis of the compound obtained in (a) or (b) above, where necessary.

The present invention further relates to a compound of the formula (IV) and a salt thereof as reactive intermediates.

The present invention moreover relates to a pharmaceutical composition containing the aforementioned pyridothiazineacetic acid compound or a pharmaceutically acceptable salt thereof, particularly to an aldose reductase inhibitor and a preparation for the prevention and treatment of the complications of diabetes.

The compound of the present invention of the formula (I) [hereinafter sometimes referred to as Compound (I)] has a novel structure essentially comprising pyrido[1,4] thiazineacetic acid moiety as a basic structure.

Each symbol used in the present specification is explained in the following.

The halogen atom at $R^1$–$R^4$ and W is fluorine atom, chlorine atom, bromine atom or iodine atom.

The lower alkyl at $R^1$–$R^4$ and $R^6$ is a straight or branched alkyl having 1 to 6 carbon atoms, such as methyl, ethyl, propyl, isopropyl, butyl, isobutyl, sec-butyl, tert-butyl, pentyl, isopentyl, sec-pentyl, tert-pentyl, hexyl, isohexyl, sec-hexyl and tert-hexyl. These lower alkyls may be substituted by aryl, amino, halogen atom (those described above) and the like.

The esterified carboxyl at $R^5$ and $R^{5'}$ is, for example, lower alkoxycarbonyl such as methoxycarbonyl, ethoxycarbonyl, propoxycarbonyl, isopropoxycarbonyl, butoxycarbonyl, isobutoxycarbonyl and tert-butoxycarbonyl, aryloxycarbonyl which may have substituent on the benzene ring, or benzyloxycarbonyl. Examples of the substituents for the aryloxycarbonyl which may have substituent on the benzene ring include halogen atom (those mentioned above), alkyl (those mentioned above), alkoxyl and nitro.

The substituted phenyl of the substituted or unsubstituted phenyl at $R^6$ is phenyl having 1 to 3 substituents selected from the group of lower alkyl (those mentioned above), halogen atom (those mentioned above) and nitro. Preferred substituents are methyl, chlorine atom and nitro.

$R^1$, $R^2$ and $R^3$ in the formula (I) can take optional positions from 4–7 positions of benzothiazole, with preference given to 4-, 5- and 7-positions. $R^4$ can take optional position from 5–8 positions of pyridothiazine ring (i.e. bonded to carbon atom), with preference given to 6- or 7-position.

A compound of the formula (I) wherein at least one of $R^1$, $R^2$ and $R^3$ is fluorine atom and $R^5$ is carboxyl is preferable.

The Compound (I) of the present invention has asymmetric carbon atom and can exist as stereoisomers, which are also encompassed in the present invention. Where necessary, the isomers can be resolved into pure isomers by conventional methods.

The pharmaceutically acceptable salts of the Compound (I) of the present invention include, for example, salts with inorganic base such as alkali metal (e.g. lithium, sodium, potassium), alkaline earth metal (e.g. calcium, magnesium, beryllium) and aluminum, and salts with organic base such as triethylamine and pyridine.

Examples of the salts of the compound of the formula (IV) include acid addition salts with inorganic acid such as hydrochloric acid, hydrobromic acid, sulfuric acid and phosphoric acid and with organic acid such as formic acid, acetic acid, trifluoroacetic acid, benzenesulfonic acid and p-toluenesulfonic acid.

The representative Compounds (I) of the present invention are the following compounds.

methyl 2-[4-(benzothiazol-2-yl)methyl-3-oxo-3,4-dihydro-2H-pyrido[2,3-b ][1,4]thiazin-2-yl]acetate 2-[4-(benzothiazol-2-yl)methyl-3-oxo-3,4-dihydro-2H-pyrido[2,3-b][1,4]thiazin-2-yl]acetic acid 2-[4-(4-fluorobenzothiazol-2-yl)methyl-3-oxo-3,4-dihydro-2H-pyrido[2,3-b][1,4]thiazin-2-yl]acetic acid ethyl 2-[4-(5-fluorobenzothiazol-2-yl)methyl-3-oxo-3,4-dihydro-2H-pyrido[2,3-b][1,4]thiazin-2-yl]acetate 2-[4-(5-fluorobenzothiazol-2-yl)methyl-3-oxo-3,4-dihydro-2H-pyrido[2,3-b][1,4]thiazin-2-yl]acetic acid 2-[4-(6-fluorobenzothiazol-2-yl)methyl-3-oxo-3,4-dihydro-2H-pyrido[2,3-b][1,4]thiazin-2-yl]acetic acid 2-[4-(7-fluorobenzothiazol-2-yl)methyl-3-oxo-3,4-dihydro-2H-pyrido[2,3-b][1,4]thiazin-2-yl]acetic acid 2-[4-(4-chlorobenzothiazol-2-yl)methyl -3-oxo-3,4-dihydro-2H-pyrido[2,3-b][1,4]thiazin-2-yl]acetic acid 2-[4-(5-chlorobenzothiazol-2-yl)methyl -3-oxo-3,4-dihydro-2H-pyrido[2,3-b][1,4]thiazin-2-yl]acetic acid 2-[4-(5-bromobenzothiazol-2-yl )methyl-3-oxo-3,4-dihydro-2H-pyrido[2,3-b][1,4]thiazin-2-yl]acetic acid ethyl 2-[4-(4,5-difluorobenzothiazol-2-yl)methyl-3-oxo-3,4-dihydro-2H-pyrido[2,3-b][1,4]thiazin-2-yl]acetate 2-[4-(4,5-difluorobenzothiazol-2-yl)methyl-3-oxo-3,4-dihydro-2H-pyrido[2,3-b][1,4]thiazin-2-yl]acetic acid 2-[4-(4,6-difluorobenzothiazol-2-yl)methyl-3-oxo-3,4-dihydro-2H-pyrido[2,3-b][1,4]thiazin-2-yl]acetic acid ethyl 2-[4-(4,7-difluorobenzothiazol-2-yl)methyl-3-oxo-3,4-dihydro-2H-pyrido[2,3-b][1,4]thiazin-2-yl]acetate 2-[4-(4,7-difluorobenzothiazol-2-yl)methyl-3-oxo-3,4-dihydro- 2H-pyrido[2,3-b][1,4]thiazin-2-yl]acetic acid 2-[4-(5,6-difluorobenzothiazol-2-yl)methyl-3-oxo-3,4-dihydro-2H-pyrido[2,3-b][1,4]thiazin-2-yl]acetic acid ethyl 2-[4-(5,7-difluorobenzothiazol-2-yl)methyl-3-oxo-3,4-dihydro-2H-pyrido[2,3-b][1,4]thiazin-2-yl]acetate 2-[4-(5,7-difluorobenzothiazol-2-yl)methyl-3-oxo-3,4-dihydro-2H-pyrido[2,3-b][1,4]thiazin-2-yl]acetic acid ethyl 2-[4-(6,7-difluorobenzothiazol-2-yl)methyl-3-oxo-3,4-dihydro-2H-pyrido[2,3-b][1,4]thiazin-2-yl]acetate 2-[4-(6,7-difluorobenzothiazol-2-yl)methyl-3-oxo-3,4-dihydro-2H-pyrido[2,3-b][1,4]thiazin-2-yl]acetic acid ethyl 2-[4-(4,5,7-trifluorobenzothiazol-2-yl)methyl-3-oxo-3,4-dihydro-2H-pyrido[2,3-b][1,4]thiazin-2-yl] acetate 2-[4-(4,5,7-trifluorobenzothiazol-2-yl)methyl-3-oxo-3,4-dihydro-2H-pyrido[2,3-b][1,4]thiazin-2-yl]acetic acid 2-[4-(4,5,6,7-tetrafluorobenzothiazol-2-yl)methyl-3-oxo-3,4-dihydro-2H-pyrido[2,3-b][1,4]thiazin-2-yl]acetic acid ethyl 2-[4-(4,5-dichlorobenzothiazol-2-yl)methyl-3-oxo-3,4-dihydro-2H-pyrido[2,3-b][1,4]thiazin-2-yl]acetate 2-[4-(4,5-dichlorobenzothiazol-2-yl)methyl-3-oxo-3,4-dihydro-2H-pyrido[2,3-b][1,4]thiazin-2-yl]acetic acid 2-[4-(4,7-dichlorobenzothiazol-2-yl)methyl-3-oxo-3,4-dihydro-2H-pyrido[2,3-b][1,4]thiazin-2-yl ]acetic acid 2-[4-(5,7-dichlorobenzothiazol-2-yl)methyl-3-oxo-3,4-dihydro-2H-pyrido[2,3-b][1,4]thiazin-2-yl]acetic acid 2-[4-(6,7-dichlorobenzothiazol-2-yl)methyl-3-oxo-3,4-dihydro-2H-pyrido[2,3-b][1,4]thiazin-2-yl]acetic acid 2-[6-chloro-4-(4,5-difluorobenzothiazol-2-yl)methyl-3-oxo-3,4-dihydro-2H-pyrido[2,3-b][1,4]thiazin-2-yl]acetic acid 2-[7-chloro-4-(4,5-difluorobenzothiazol-2-yl)methyl-3-oxo-3,4-dihydro-2H-pyrido[2,3-b][1,4]thiazin-2-yl]acetic acid 2-[6-fluoro-4-(4,5-difluorobenzothiazol-2-yl)methyl-3-oxo-3,4-dihydro-2H-pyrido[2,3-b][1,4]thiazin-2-yl]acetic acid ethyl 2-[7-fluoro-4-(4,5-difluorobenzothiazol-2-yl)methyl-3-oxo-3,4-dihydro-2H-pyrido[2,3-b][1,4]thiazin-2-yl]acetate 2-[6-chloro-4-(4,5,7-trifluorobenzothiazol-2-yl)methyl-3-oxo-3,4-dihydro-2H-pyrido[2,3-b][1,4]thiazin-2-yl]acetic acid 2-[7-chloro-4-(4,5,7-trifluorobenzothiazol-2-yl)methyl-3-oxo-3,4-dihydro-2H-pyrido[2,3-b][1,4]thiazin-2-yl]acetic acid 2-[6-fluoro-4-(4,5,7-trifluorobenzothiazol-2-yl)methyl-3-oxo-3,4-dihydro-2H-pyrido[2,3-b][1,4]thiazin-2-yl]acetic acid 2-[7-fluoro-4-(4,5,7-trifluorobenzothiazol-2-yl)methyl-3-oxo-3,4-dihydro-2H-pyrido[2,3-b][1,4]thiazin-2-yl]acetic acid 2-[4-(benzothiazol-2-yl)methyl-3-oxo-3,4-dihydro-2H-pyrido[3,2-b][1,4]thiazin-2-yl]acetic acid 2-[4-(4-fluorobenzothiazol-2-yl)methyl-3-oxo-3,4-dihydro-2H-pyrido[3,2-b][1,4]thiazin-2-yl]acetic acid 2-[4-(5-fluorobenzothiazol-2-yl)methyl-3-oxo-3,4-dihydro-2H-pyrido[3,2-b][1,4]thiazin-2-yl]acetic acid 2-[4-(7-fluorobenzothiazol-2-yl)methyl-3-oxo-3,4-dihydro-2H-pyrido[3,2-b][1,4]thiazin-2-yl]acetic acid 2-[4-(5-chlorobenzothiazol-2-yl)methyl-3-oxo-3,4-dihydro-2H-pyrido[3,2-b][1,4]thiazin-2-yl]acetic acid 2-[4-(4,5-difluorobenzothiazol-2-yl)methyl-3-oxo-3,4-dihydro-2H-pyrido[3,2-b][1,4]thiazin-2-yl]acetic acid 2-[4-(5,7-difluorobenzothiazol-2-yl)methyl-3-oxo-3,4-dihydro-2H-pyrido[3,2-b][1,4]thiazin-2-yl]acetic acid 2-[4-(6,7-difluorobenzothiazol-2-yl)methyl-3-oxo-3,4-dihydro-2H-pyrido[3,2-b][1,4]thiazin-2-yl]acetic acid 2-[4-(4,5,7-trifluorobenzothiazol-2-yl)methyl-3-oxo-3,4-dihydro-2H-pyrido[3,2-b][1,4]thiazin-2-yl]acetic acid 2-[4-(4,5-dichlorobenzothiazol-2-yl)methyl-3-oxo-3,4-dihydro-2H-pyrido[3,2-b][1,4]thiazin-2-yl]acetic acid 2-[4-(benzothiazol-2-yl)methyl-7-chloro-3-oxo-3,4-dihydro-2H-pyrido[3,2-b][1,4]thiazin-2-yl]acetic acid 2-[7-chloro-4-(4-fluorobenzothiazol-2-yl)methyl-3-oxo-3,4-dihydro-2-H-pyrido[3,2-b][1,4]thiazin-2-yl]acetic acid 2-[7-chloro-4-(5-fluorobenzothiazol-2-yl)methyl-3-oxo-3,4-dihydro-2H-pyrido[3,2-b][1,4]thiazin-2-yl]acetic acid 2-[7-chloro-4-(7-fluorobenzothiazol-2-yl)methyl-3-oxo-3,4-dihydro-2H-pyrido[3,2-b][1,4]thiazin-2-yl]acetic acid 2-[7-chloro-4-(5-chlorobenzothiazol-2-yl)methyl-3-oxo-3,4-dihydro-2H-pyrido[3,2-b][1,4]thiazin-2-yl]acetic acid 2-[7-chloro-4-(4,5-difluorobenzothiazol-2-yl)methyl-3-oxo-3,4-dihydro-2H-pyrido[3,2-b][1,4]thiazin-2-yl]acetic acid 2-[7-chloro-4-(5,7-difluorobenzothiazol-2-yl)methyl-3-oxo-3,4-dihydro-2H-pyrido[3,2-b][1,4]thiazin-2-yl]acetic acid 2-[7-chloro-4-(6,7-difluorobenzothiazol-2-yl)methyl-3-oxo-3,4-dihydro-2H-pyrido[3,2-b][1,4]thiazin-2-yl]acetic acid ethyl 2-[7-chloro-4-(4,5,7-trifluorobenzothiazol-2-yl)methyl-3-oxo-3,4-dihydro-2H-pyrido[3,2-b][1,4]thiazin-2-yl]acetate 2-[7-chloro-4-(4,5,7-trifluorobenzothiazol-2-yl)methyl-3-oxo-3,4-dihydro-2H-pyrido[3,2-b][1,4]thiazin-2-yl]acetic acid 2-[7-chloro-4-(4,5-dichlorobenzothiazol-2-yl)methyl-3-oxo-3,4-dihydro-2H-pyrido[3,2-b][1,4]thiazin-2-yl]acetic acid 2-[7-fluoro-4-(4,5,7-trifluorobenzothiazol-2-yl)methyl-3-oxo-3,4-dihydro-2H-pyrido[3,2-b][1,4]thiazin-2-yl]acetic acid 2-[4-(benzothiazol-2-yl)methyl-3-oxo-3,4-dihydro-2H-pyrido[3,4-b][1,4]thiazin-2-yl]acetic acid 2-[4-(4-fluorobenzothiazol-2-yl)methyl-3-oxo-3,4-dihydro-2H-pyrido[3,4-b][1,4]thiazin-2-yl]acetic acid 2-[4-(5-fluorobenzothiazol-2-yl)methyl-3-oxo-3,4-dihydro-2H-pyrido[3,4-b][1,4]thiazin-2-yl]acetic acid 2-[4-(7-fluorobenzothiazol-2-yl)methyl-3-oxo-3,4-dihydro-2H-pyrido[3,4-b][1,4]thiazin-2-yl]acetic acid 2-[4-(5-chlorobenzothiazol-2-yl)methyl-3-oxo-3,4-dihydro-2H-pyrido[3,4-b][1,4]thiazin-2-yl]acetic acid 2-[4-(4,5-difluorobenzothiazol-2-yl)methyl-3-oxo-3,4-dihydro-2H-pyrido[3,4-b][1,4]thiazin-2-yl]acetic acid 2-[4-(5,7-difluorobenzothiazol-2-yl)methyl-3-oxo-3,4-dihydro-2H-pyrido[3,4-b][1,4]thiazin-2-yl]acetic acid 2-[4-(6,7-difluorobenzothiazol-2-yl)methyl-3-oxo-3,4-dihydro-2H-pyrido[3,4-b][1,4]thiazin-2-yl]acetic acid ethyl 2-[4-(4,5,7-trifluorobenzothiazol-2-yl)methyl-3-oxo-3,4-dihydro-2H-pyrido[3,4-b][1,4]thiazin-2-yl]acetate 2-[4-(4,5,7-trifluorobenzothiazol-2-yl)methyl-3-oxo-3,4-dihydro-2H-pyrido[3,4-b][1,4]thiazin-2-yl]acetic acid 2-[4-(4,5-dichlorobenzothiazol-2-yl)methyl-3-oxo-3,4-dihydro-2H-pyrido[3,4-b][1,4]thiazin-2-yl]acetic acid The production of the Compound (I) of the present invention is described in detail in the following.

Production (a)

A compound of the formula (II)

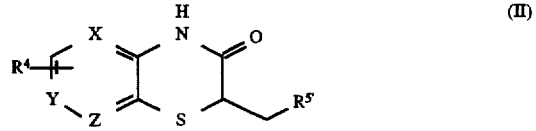

wherein $R^4$, $R^{5'}$, X, Y and Z are as defined above, or a salt thereof is reacted with a compound of the formula (III)

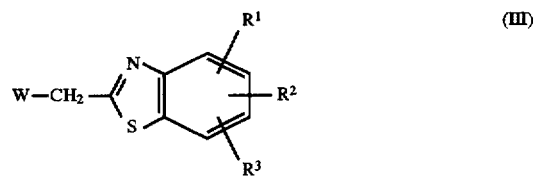

wherein $R^1$, $R^2$, $R^3$ and W are as defined above, under basic conditions and/or an inert gas atmosphere as necessary, followed by hydrolysis in the presence of a base or acid on demand to give a Compound (I) of the present invention.

The salt of the compound of the formula (II) is preferably the aforementioned pharmaceutically acceptable salt.

Examples of the base to be used for the above-mentioned basic conditions include inorganic bases such as alkali metal (e.g. lithium, sodium, potassium), alkaline earth metal (e.g. beryllium, magnesium, calcium), alkali metal hydride (e.g. sodium hydride), alkaline earth metal hydride (e.g. calcium hydride), alkali metal hydroxide (e.g. sodium hydroxide, potassium hydroxide), alkali metal carbonate (e.g. sodium carbonate, potassium carbonate), alkali metal hydrogencarbonate (e.g. sodium hydrogencarbonate, potassium hydrogencarbonate), alkali metal alkoxide (e.g. sodium methoxide, sodium ethoxide, potassium tert-butoxide) and alkali metal alkanoate (e.g. sodium acetate) and organic bases such as trialkylamine (e.g. triethylamine), pyridine compound (e.g. pyridine, lutidine, picoline, 4-dimethylaminopyridine) and quinoline.

The inert gas includes, for example, nitrogen, argon and helium.

The above-mentioned reaction is generally carried out in various conventional solvents such as those which do not exert adverse influences on the reaction (e.g. dichloromethane, methanol, ethanol, propanol, pyridine, N,N-dimethylformamide, tetrahydrofuran, dimethylsulfoxide) and a mixture thereof. The preferable solvent is, for example, N,N-dimethylformamide, tetrahydrofuran or dimethylsulfoxide.

While the reaction temperature is not particularly limited, it is generally from under cooling to under heating. When sodium hydride is used as a base, for example, the reaction temperature is preferably from −30° C. to room temperature.

The preferable base to be used for the hydrolysis includes, for example, alkali metal hydroxides such as sodium hydroxide and potassium hydroxide and alkali metal carbonates such as sodium carbonate and potassium carbonate. The preferable acid includes, for example, organic acids such as formic acid, acetic acid, propionic acid, trifluoroacetic acid, benzenesulfonic acid and p-toluenesulfonic acid and inorganic acids such as hydrochloric acid, hydrobromic acid, sulfuric acid and phosphoric acid.

The hydrolysis is carried out in a conventional solvent which does not exert adverse influences on the reaction, such as water acetone, dioxane, dichloromethane, methanol, ethanol, propanol, pyridine, N,N-dimethylformamide and a mixture thereof. When the base or acid to be used for the reaction is liquid, it may be used as a solvent.

The reaction temperature for hydrolysis is not particularly limited and the reaction is carried out at a temperature from under cooling to under heating.

The starting compound of the formula (II) is known or can be produced easily by a known method [Chemical Abstracts, 103, 6291n, 568 (1985), Japanese Patent Unexamined Publication No. 8387/1988].

The starting compound of the formula (III) is known or can be produced easily by a known method [Journal of Medicinal Chemistry, 34, 108–122 (1991)].

Production (b)

A compound of the formula (IV)

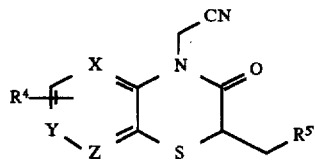

(IV)

wherein $R^4$, $R^{5'}$, X, Y and Z are as defined above, or an acid addition salt thereof is reacted with a compound of the formula (V)

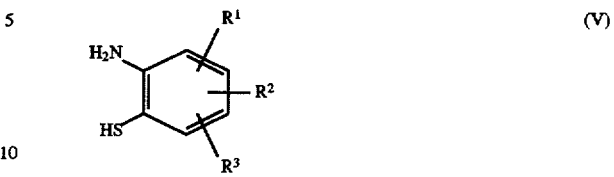

(V)

wherein $R^1$, $R^2$ and $R^3$ are as defined above, or an acid addition salt thereof, followed by, where necessary, hydrolysis in the presence of a base or acid to give a Compound (I) of the present invention.

Note that when the compounds of the formulas (IV) and (V) are not acid addition salts when added to each other, the reaction needs to be done in the presence of a strong acid.

Examples of the acid addition salts of the compounds of the formulas (IV) and (V) include acid addition salts with inorganic acid such as hydrochloric acid, hydrobromic acid, sulfuric acid and phosphoric acid, and with organic acid such as formic acid, acetic acid, trifluoroacetic acid, benzenesulfonic acid and p-toluenesulfonic acid.

Examples of the strong acid include sulfuric acid and hydrochloric acid.

The particularly preferable solvent in the aforementioned reaction includes, for example, methanol, ethanol and propanol. In this case, the reaction temperature is preferably from 60° C. to refluxing temperature.

When a solvent is not used, the compound of the formula (IV) may be subjected to eutectic reaction with an acid addition salt (e.g. hydrochloric acid) of the compound of the formula (V) at a temperature between 130° C. and 180° C. to allow reaction.

Examples of the base preferably used for the hydrolysis include alkali metal hydroxides such as sodium hydroxide and potassium hydroxide and alkali metal carbonates such as sodium carbonate and potassium carbonate. Preferable acid includes, for example, organic acids such as formic acid, acetic acid, propionic acid, trifluoroacetic acid, benzenesulfonic acid and p-toluenesulfonic acid and inorganic acids such as hydrochloric acid, hydrobromic acid, sulfuric acid and phosphoric acid.

The hydrolysis is generally carried out in a conventional solvent which does not exert adverse influences on the reaction, such as water, acetone, dioxane, dichloromethane, methanol, ethanol, propanol, pyridine, N,N-dimethylformamide and a mixture thereof. When the base or acid to be used for the reaction is liquid, it may be used as a solvent.

The reaction temperature for the hydrolysis is not particularly limited and the reaction is carried out at a temperature from under cooling to under heating.

The starting compound of the formula (IV) can be obtained by reacting a compound of the formula (II) with a compound of the formula (VI)

U—CH$_2$CN   (VI)

wherein U is halogen atom (those mentioned above), under suitable basic conditions and/or an inert gas atmosphere.

Examples of the base to be used for the aforementioned basic conditions include alkali metal hydrides such as sodium hydride, alkaline earth metal hydrides such as calcium hydride, alkali metal hydroxides such as sodium hydroxide and potassium hydroxide, alkali metal carbonates such as sodium carbonate and potassium carbonate, alkali metal hydrogencarbonates such as sodium hydrogencarbonate and potassium hydrogencarbonate, alkali metal alkoxides such as sodium methoxide, sodium ethoxide and potassium tert-butoxide and alkali metal alkanates such as sodium acetate.

The inert gas includes, for example, nitrogen, argon and helium.

The above-mentioned reaction is generally carried out in various conventional solvents such as those which do not exert adverse influences on the reaction (e.g. dichloromethane, methanol, ethanol, propanol, pyridine, N,N-dimethylformamide, tetrahydrofuran, dimethylsulfoxide) and a mixture thereof. The preferable solvent is, for example, N,N-dimethylformamide, tetrahydrofuran or dimethylsulfoxide.

While the reaction temperature is not particularly limited, it is preferably from room temperature to 100° C.

The starting compound of the formula (V) is known or can be produced easily by a known method [Journal of Medicinal Chemistry, 34, 108–122 (1991)].

By the above-mentioned production, the Compound (I) of the present invention can be efficiently produced.

The Compound (I) of the present invention obtained by the above-mentioned production can be isolated and purified by conventional methods such as extraction, precipitation, fractional chromatography, partition, crystallization and recrystallization.

When desired, the Compound (I) of the present invention thus produced can be converted to the aforementioned pharmaceutically acceptable salt by conventional methods.

The results of the pharmacological test to show the effectiveness of the compound (I) of the present invention are given in the following. The similar results were also obtained with regard to the compounds of the present invention that are not exemplified here.

1) Aldose Reductase Inhibitory Action

Preparation of Enzyme

An aldose reductase enzyme standard product was prepared from swine lens according to the method of S. Hayman et al. [Journal of Biological Chemistry, 240, 877–882 (1965)]. That is, swine lenses freeze-stored at −80° C. were homogenized with distilled water and cetrifuged at 10,000 G for 15 minutes. The supernatant was prepared into a 40% ammonium sulfate solution and subjected to cetrifugation at 10,000 G for 10 minutes. The supernatant obtained was dialyzed overnight against a 0.05M sodium chloride solution to give a dialyzed solution, which was used as an enzyme standard product.

Activity Determination

Test drugs: Compound of the invention and EPALRESTAT (described in Japanese Patent Unexamined Publication No. 40478/1982)

The activity of aldose reductase was determined by the above-mentioned method of S. Hayman et al. That is, the above-mentioned enzyme solution (25 μl) and a drug solution (25 μl) dissolved in 1% DMSO at various concentrations were added to a 40 mM phosphate buffer (200 μl, pH 6.2) containing final concentrations of 0.4M lithium sulfate, 0.1 mM NADPH (reduced type nicotinamide adenine dinucleotide phosphate) and 3 mM di-glyceraldehyde as a substrate. The mixture was allowed to react at 25° C. for 2 minutes and the changes in absorbance at 340 nm were determined with COBAS FARA II (manufactured by Roche). The changes in absorbance when 1% DMSO was added instead of the drug solution was taken as 100%, based on which 50% inhibition concentration ($IC_{50}$) was calculated and shown in Table 1. The test drug number indicates the example number to be mentioned later. $IC_{50}$ (M) shows the concentration of the drug inhibiting the aldose reductase activity by 50%.

TABLE 1

| Test drug | $IC_{50}$ (M) |
|---|---|
| Compound of Ex. 9 | $1.1 \times 10^{-8}$ |
| Compound of Ex. 10 | $1.2 \times 10^{-8}$ |
| Compound of Ex. 12 | $1.2 \times 10^{-8}$ |
| Compound of Ex. 13 | $1.4 \times 10^{-8}$ |
| Compound of Ex. 14 | $1.2 \times 10^{-8}$ |
| EPALRESTAT | $2.1 \times 10^{-8}$ |

2) Inhibitory action on sorbitol accumulation in tissues of rats with experimental diabetes Test Drugs: Compound of Example 9 and EPALRESTAT (described in Japanese Patent Unexamined Publication No. 40478/1982)

Sprague-Dawley rats (male, 6 weeks old, 5–6 per group) were fasted for 18 hours and injected with streptozotocin (SIGMA, 60 mg/kg) via the tail vein under etherization to prepare rats with diabetes.

The test drugs were orally administered at 4, 8 and 24 hours after the injection of streptozotocin. The compound of Example 9 was administered at 10 mg/kg and EPALRESTAT was administered at 30 mg/kg as a 0.5% carboxymethylcellulose suspension, respectively. During the administrations, the rats were raised under free access to feed and water and the sorbitol content in the tissues (erythrocytes, sciatic nerve, lens) was determined 3 hours after the final administration, according to the enzyme method of H. Y. Bergmeyer et al. [Methods of Enzymatic Analysis, vol. 3, 1323–1330 (1974)] with the use of SDH (sorbitol dehydrogenase) and NAD (β-nicotinamide adenine dinucleotide). The results (sorbitol accumulation) are expressed in percent (%) relative to the value of a control group administered with a 0.5% carboxymethylcellulose solution (solvent) instead of the drug, which was taken as 100%. The results are shown in Table 2.

TABLE 2

| Test drug (mg/kg) | Sorbitol accumulation (%)[1] | | |
|---|---|---|---|
| | erythrocytes | nerve | lens |
| Compound of Example 9 (10) | 59.0* | 3.3* | 66.2* |
| EPALRESTAT (30) | 66.5 | 99.9 | 89.1 |

[1]The control was taken as 100%.
*Tukey's Multiple Range Test: * $p < 0.01$

The acute toxicity of the single dose of the compound of the present invention was confirmed by the following test.

Normal ICR mice (male, 7 weeks old, 5 per group) were fasted for 18 hours and the compound (300 mg/kg) of Example 9 was orally administered as a 0.5% carboxymethylcellulose suspension. To the control group, a 0.5% carboxymethylcellulose solution alone was orally administered and observation was continued for 14 days thereafter, during which period the mice were allowed to take feed and water freely.

There was no death case among the mice administered with the compound of the present invention and their weights showed transition in the same manner as in the control group.

As mentioned above, the compound of the present invention and a pharmaceutically acceptable salt thereof have a superior aldose reductase inhibitory action on mammals inclusive of human, cow, horse, dog, mouse, rat and so on and show superior safety. Accordingly, they are effectively used for the prevention and treatment of the complications of diabetes, such as faulty union of corneal injury, cataract, neurosis, retinopathy and nephropathy, particularly for the prevention and treatment of cataract and neurosis.

When the compound of the present invention and a pharmaceutically acceptable salt thereof are administered for the prevention and/or treatment of the above-mentioned diseases, oral or parenteral administration can be employed.

The compound of the present invention and a pharmaceutically acceptable salt thereof are provided in the form of a solid preparation, semi-solid preparation or liquid preparation together with organic or inorganic carrier and/or excipient suitable for external, oral or local administration. The compound of the present invention and salts thereof are used for the provision of a suitable dosage form such as tablet, pellet, capsule, suppository, liquid, emulsion or suspension along with nontoxic and pharmacologically acceptable auxiliary ingredients. The auxiliary ingredients include, for example, those effectively used for the production of solid, semi-solid or liquid preparations, such as water, glucose, lactose, gelatin, mannitol, starch paste, magnesium trisillicate, corn starch, keratin, colloidal silica, potato starch and urea. In addition, the auxiliary ingredients include stabilizer, extender, coloring and aromatic agent. So as to retain the activity of the compound of the present invention and salts thereof, a preservative may be also contained. The pharmaceutical preparation should contain the compound of the present invention or a salt thereof in an amount sufficient to produce the desired therapeutic effect against the progress or symptom of the target diseases.

When the compound of the present invention or a pharmaceutically acceptable salt thereof is administered to human, it is preferably administered, for example, as an injection or eye drop, or orally in an amount sufficient to inhibit aldose reductase or an amount sufficient to prevent and/or treat the complications of diabetes.

While the dose of the compound of the present invention or a salt thereof varies depending on age, body weight, symptom, preventive and therapeutic effect, administration route, administration period etc., the compound or a salt is generally administered orally at 1–2000 mg/day, preferably at 10–600 mg/day in a single to thrice divided doses a day.

The present invention is explained in more detail in the following by way of examples, to which the present invention is not limited.

EXAMPLE 1

Ethyl 2-[4-(5-fluorobenzothiazol-2-yl)methyl-3-oxo-3,4-dihydro-2H-pyrido[2,3-b][1,4]thiazin-2-yl]acetate Ethyl 2-(3-oxo-3,4-dihydro-2H-pyrido[2,3-b][1,4]thiazin-2-yl)acetate (252 mg), potassium carboante (166 mg) and potassium iodide (20 mg) were dissolved in dimethylsulfoxide (3 ml) and the mixture was stirred for 15 minutes. 2-Bromomethyl-5-fluorobenzothiazole (295 mg) was added and the mixture was stirred at room temperature overnight. A saturated aqueous solution of ammonium chloride was added to the reaction mixture and the mixture was extracted with ethyl acetate. The organic layer was washed with a saturated aqueous solution of sodium chloride and dried over anhydrous magnesium sulfate, followed by evaporation of the solvent. The obtained semicrystal residue was dissolved in benzene and an insoluble matter was filtered off. Then, the solvent was distilled away. The obtained oily residue was subjected to silica gel chromatography and eluted with toluene-ethyl acetate to give 296 mg of the title compound. The physical properties of the compound are given in the following.

MS (EI, m/z): 417 [M$^+$]

NMR (CDCl$_3$, δ): 1.29 (3H, t), 2.69 (1H, dd), 3.14 (1H, dd), 4.18 (1H, dd), 4.22 (2H, q), 5.39 (1H, d), 5.59 (1H, d), 7.15–8.25 (6H)

EXAMPLE 2

Ethyl 2-[4-(4,5,7-trifluorobenzothiazol-2-yl)methyl-3-oxo-3,4-dihydro-2H-pyrido[2,3-b][1,4]thiazin-2-yl]acetate A mixture of ethyl 2-(4-cyanomethyl-3-oxo-3,4-dihydro-2H-pyrido[2,3-b][1,4]thiazin-2-yl]acetate (790 mg) and 2-amino-3,4,6-trifluorothiophenol hydrochloride (612 mg) was heated at 180° C. for 30 minutes for melting. After cooling, water was added to the residue and the mixture was extracted with ethyl acetate. The organic layer was washed with a saturated aqueous solution of sodium chloride and dried over anhydrous magnesium sulfate, and the solvent was distilled away. Isopropyl ether was added to the residue to allow crystallization, whereby 815 mg of the title compound was obtained. The physical properties of the compound are given in the following.

MS (EI, m/z): 453 [H$^+$]

NMR (CDCl$_3$, δ): 1.29 (3H, t), 2.70 (1H, dd), 3.14 (1H, dd), 4.17 (1H, dd), 4.22 (2H, q), 5.43 (1H, d), 5.59 (1H, d), 7.03–8.25 (4H)

In the following Examples 3–6, the title compounds were obtained in substantially the same manner as in Example 2.

EXAMPLE 3

Ethyl 2-[4-(4,5-difluorobenzothiazol-2-yl)methyl-3-oxo-3,4-dihydro-2H-pyrido[2,3-b][1,4]thiazin-2-yl]acetate MS (EI, m/z): 435 [M$^+$]

NMR (CDCl$_3$, δ): 1.29 (3H, t), 2.70 (1H, dd), 3.14 (1H, dd), 4.17 (1H, dd), 4.22 (2H, q), 5.43 (1H, d), 5.61 (1H, d), 7.19–8.23 (5H)

EXAMPLE 4

Ethyl 2-[4-(5,7-difluorobenzothiazol-2-yl)methyl-3-oxo-3,4-dihydro-2H-pyrido[2,3-b][1,4]thiazin-2-yl]acetate MS (EI, m/z): 435 [M$^+$]

NMR (CDCl$_3$, δ): 1.28 (3H, t), 2.69 (1H, dd), 3.14 (1H, dd), 4.18 (1H, dd), 4.22 (2H, q), 5.39 (1H, d), 5.57 (1H, d), 6.95–8.24 (5H)

EXAMPLE 5

Ethyl 2-[4-(4,5-dichlorobenzothiazol-2-yl)methyl-3-oxo-3,4-dihydro-2H-pyrido[2,3-b][1,4]thiazin-2-yl]acetate MS (EI, m/z): 469, 467 [M$^+$]

NMR (CDCl$_3$, δ): 1.29 (3H, t), 2.70 (1H, dd), 3.14 (1H, dd), 4.17 (1H, dd), 4.22 (2H, q), 5.48 (1H, d), 5.62 (1H, d), 7.19–8.23 (5H)

EXAMPLE 6

Ethyl 2-[7-chloro-4-(4,5,7-trifluorobenzothiazol-2-yl)-methyl-3-oxo-3,4-dihydro-2H-pyrido[3,2-b][1,4]thiazin-2-yl]acetate MS (EI, m/z): 489, 487 [M$^+$]

NMR (CDCl$_3$, δ): 1.28 (3H, t), 2.66 (1H, dd), 3.15 (1H, dd), 4.16 (1H, dd), 4.21 (2H, q), 5.74 (1H, d), 5.86 (1H, d), 6.96–8.18 (3H)

EXAMPLE 7

Ethyl 2-[4-(4,5,7-trifluorobenzothiazol-2-yl)methyl-3-oxo-3,4-dihydro-2H-pyrido[3,4-b][1,4]thiazin-2-yl]acetate Ethyl 2-(4-eyanomethyl-3-oxo-3,4-dihydro-2H-pyrido[3,4-b][1,4]thiazin-2-yl)acetate (303 mg) and 2-amino-3,4,6-trifluorothiophenol hydrochloride (315 mg) were added to absolute ethanol (3 ml) and the mixture was refluxed under heating under an argon atmosphere. Eighteen hours later, the solvent was distilled away and water was added to the residue. The mixture was extracted with ethyl acetate. The organic layer was washed with a saturated aqueous solution of sodium chloride and dried over anhydrous magnesium sulfate, and the solvent was distilled-away. The obtained oily residue was subjected to silica gel column chromatography and eluted with toluene-ethyl acetate to give 380 mg of the title compound. The physical properties of the compound are given in the following.

MS (EI, m/z): 453 [M$^+$]

NMR (CDCl$_3$, δ): 1.29 (3H, t), 2.66 (1H, dd), 3.11 (1H, dd), 4.09 (1H, dd), 4.22 (2H, q), 5.53 (1H, d), 5.61 (1H, d), 7.03–8.56 (4H)

EXAMPLE 8

2-[4-(5-Fluorobenzothiazol-2-yl)methyl-3-oxo-3,4-dihydro-2H-pyrido[2,3-b][1,4]thiazin-2-yl]acetic acid The compound (276 mg) of Example 1 was added to a 47% hydrobromic acid solution and the mixture was refluxed under heating for 4 hours. After cooling, the mixture was diluted with water and extracted with ethyl acetate. The organic layer was washed with a saturated aqueous solution of sodium chloride and dried over anhydrous magnesium sulfate, and the solvent was distilled away. Ethyl acetate was added to the residue to allow crystallization, whereby 226 mg of the title compound was obtained. The physical properties of the compound are given in the following.

MS (EI, m/z): 389 [M$^+$]

IR (KBr, cm$^{-3}$): 2550–3120, 1680

NMR (CDCl$_3$, δ): 2.74 (1H, dd), 3.21 (1H, dd), 4.17 (1H, t), 5.43 (1H, d), 5.59 (1H, d), 7.14–8.25 (6H)

In the following Examples 9–14, the title compounds were obtained in substantially the same manner as in Example 8.

EXAMPLE 9

2-[4-(4,5,7-Trifluorobenzothiazol-2-yl)methyl-3-oxo-3,4-dihydro-2H-pyrido[2,3-b][1,4]thiazin-2-yl] acetic acid MS (EI, m/z): 425 [M$^+$]

IR (KBr, cm$^{-1}$): 2480–3070, 1690

NMR (CDCl$_3$, δ): 2.76 (1H, dd), 3.21 (1H, dd), 4.16 (1H, t), 5.44 (1H, d), 5.61 (1H, d), 7.02–8.27 (4H)

EXAMPLE 10

2-[4-(4,5-Difluorobenzothiazol-2-yl)methyl-3-oxo-3,4-dihydro-2H-pyrido[2,3-b][1,4]thiazin-2-yl]acetic acid MS (EI, m/z): 407 [M$^+$]

IR (KBr, cm$^{-1}$): 2540–3120, 1720, 1680

NMR (CDCl$_3$, δ): 2.75 (1H, dd), 3.21 (1H, dd), 4.16 (1H, t), 5.46 (1H, d), 5.61 (1H, d), 7.23–8.25 (5H)

EXAMPLE 11

2-[4-(5,7-Difluorobenzothiazol-2-yl)methyl-3-oxo-3,4-dihydro-2H-pyrido[2,3-b][1,4]thiazin-2-yl]acetic acid MS (EI, m/z): 407 [M$^+$]

IR (KBr, cm$^{-1}$): 2530–3100, 1720, 1690

NMR (CDCl$_3$, δ): 2.75 (1H, dd), 3.22 (1H, dd), 4.16 (1H, t), 5.40 (1H, d), 5.59 (1H, d), 6.91–8.27 (5H)

EXAMPLE 12

2-[4-(4,5-Dichlorobenzothiazol-2-yl)methyl-3-oxo-3,4-dihydro-2H-pyrido[2,3-b][1,4]thiazin-2-yl]acetic acid MS (EI, m/z): 441, 439 [M$^+$]

IR (KBr, cm$^{-1}$): 2560–3600, 1730, 1680

NMR (CDCl$_3$, δ): 2.75 (1H, dd), 3.21 (1H, dd), 4.16 (1H, t), 5.50 (1H, d), 5.62 (1H, d), 7.22–8.25 (5H)

EXAMPLE 13

2-[7-Chloro-4-(4,5,7-trifluorobenzothiazol-2-yl)methyl-3-oxo-3,4-dihydro-2H-pyrido[2,3-b][1,4]thiazin-2-yl]acetic acid MS (EI, m/z): 461, 459 [M$^+$]

IR (KBr, cm$^{-1}$): 2600–3100, 1720, 1690

NMR (CDCl$_3$, δ): 2.74 (1H, dd), 3.22 (1H, dd), 4.14 (1H, dd), 5.73 (1H, d), 5.87 (1H, d), 6.96–8.19 (3H)

EXAMPLE 14

2-[4-(4,5,7-Trifluorobenzothiazol-2-yl)methyl-3-oxo-3,4-dihydro-2H-pyrido[3,4-b][1,4]thiazin-2-yl] acetic acid MS (EI, m/z): 425 [M$^+$]

IR (KBr, cm$^{-1}$): 2500–3100, 1715

NMR (CDCl$_3$, δ): 2.64 (1H, dd), 3.11 (1H, dd), 4.08 (1H, dd), 5.54 (1H, d), 5.62 (1H, d), 7.04–8.57 (4H)

EXAMPLE 15

Ethyl 2-(4-cyanomethyl-3-oxo-3,4-dihydro-2H-pyrido[2,3-b][1,4]thiazin-2-yl]acetate Ethyl 2-(3-oxo-3,4-dihydro-2H-pyrido[2,3-b][1,4]thiazin-2-yl)acetate (8.40 g), bromoacetonitrile (6.00 g) and potassium iodide (664 mg) were dissolved in dimethylsulfoxide (20 ml). Thereto was added potassium carbonate (6.91 g) and the mixture was stirred at room temperature for 40 hours. A saturated aqueous solution of ammonium chloride was added to the reaction mixture and the mixture was extracted with ethyl acetate. The organic layer was washed with a saturated aqueous solution of sodium chloride and dried over anhydrous magnesium sulfate, and the solvent was distilled away. Benzene was added to the residue and an insoluble matter was filtered off, followed by evaporation of the solvent. The obtained oily residue was subjected to silica gel column chromatography and eluted with toluene-ethyl acetate to give 6.88 g of the title compound. The physical properties of the compound are given in the following.

MS (EI, m/z): 291 [M⁺]

NMR (CDCl₃, δ): 1.24 (3H, t), 2.68 (1H, dd), 3.09 (1H, dd), 4.11 (1H, dd), 4.21 (2H, q), 4.71 (1H, d), 4.95 (1H, d), 7.30–8.31 (3H)

In the following Examples 16 and 17, the title compounds were obtained in substantially the same manner as in Example 15.

EXAMPLE 16

Ethyl 2-(7-chloro-4-cyanomethyl-3-oxo-3,4-dihydro-2H-pyrido[2,3-b][1,4]thiazin-2-yl)acetate MS (EI, m/z): 327, 325 [M⁺]

NMR (CDCl₃, δ): 1.29 (3H, t), 2.62 (1H, dd), 3.10 (1H, dd), 4.10 (1H, dd), 4.21 (2H, q), 5.00 (1H, d), 5.11 (1H, d), 7.71 (1H, d), 8.27 (1H, d)

EXAMPLE 17

Ethyl 2-(4-cyanomethyl-3-oxo-3,4-dihydro-2H-pyrido[3,4-b][1,4]thiazin-2-yl)acetate MS (EI, m/z): 291 [M⁺]

NMR (CDCl₃, δ): 1.29 (3H, t), 2.64 (1H, dd), 3.07 (1H, dd), 4.02 (1H, dd), 4.21 (2H, q), 4.76 (1H, d), 4.96 (1H, d), 7.70–8.60 (3H)

The formulation examples are given in the following.

FORMULATION EXAMPLE 1

| Compound of Example 9 | 20 g |
|---|---|
| Lactose | 315 g |
| Corn starch | 125 g |
| Crystalline cellulose | 25 g |

The above ingredients were homogeneously mixed and added with an aqueous solution (200 ml) of 7.5% hydroxypropyl-cellulose. The mixture was prepared into granules by an extrusion granulator with the use of a 0.5 mm diameter screen. The granules were immediately rounded and dried. The dry granules were coated with a film coating solution (1.9 kg) of the following composition by a fluid-type granulator to give enteric coated granules.

Coating Solution:

| Hydroxypropylmethylcellulose phthalate | 5.0 (w/w)% |
|---|---|
| Stearic acid | 0.25 (w/w)% |
| Methylene chloride | 50.0 (w/w)% |
| Ethanol | 44.75 (w/w)% |

FORMULATION EXAMPLE 2

| Compound of Example 10 | 20 g |
|---|---|
| Lactose | 100 g |
| Corn starch | 36 g |
| Crystalline cellulose | 30 g |
| Calcium carboxymethylcellulose | 10 g |
| Magnesium stearate | 4 g |

The above ingredients were homogeneously mixed and prepared by a single punch tableting machine into tablets each weighing 200 mg with the use of a 7.5 mm diameter punch. Then, the film coating solution of the following composition was spray-coated at 10 mg per tablet to give enteric coated tablets.

Coating Solution:

| Hydroxypropylmethylcellulose phthalate | 8.0 (w/w)% |
|---|---|
| Glycerol fatty acid ester | 0.4 (w/w)% |
| Methylene chloride | 50.0 (w/w)% |
| White beewax | 0.1 (w/w)% |
| Isopropanol | 41.5 (w/w)% |

FORMULATION EXAMPLE 3

| Compound of Example 13 | 200 g |
|---|---|
| Polysorbate 80 | 20 g |
| PANASETO ® 810 | 1780 g |

The above ingredients were mixed and completely dissolved. With the use of a film solution for soft capsules composed of gelatin (100 parts), con. glycerine (30 parts), ethyl p-hydroxybenzoate (0.4 part) and propyl p-hydroxybenzoate (0.2 part), soft capsules containing 200 mg of a drug solution per capsule were prepared by a rotary method.

FORMULATION EXAMPLE 4

| Compound of Example 14 | 100 mg |
|---|---|
| Sodium acetate | 2 mg |
| Acetic acid (for adjusting to pH 5.8) | suitable amount |
| Distilled water | residual amount |
| | Total 10 ml/vial |

An injection having the above formulation was prepared by a conventional method.

FORMULATION EXAMPLE 5

| Compound of Example 9 | 0.05 g |
|---|---|
| Polysorbate 80 | 0.2 g |
| Sodium dihydrogenphosphate 2 hydrate | 0.2 g |
| Disodium hydrogenphosphate 12 hydrate | 0.5 g |
| Sodium chloride | 0.75 g |
| Methyl p-hydroxybenzoate | 0.026 g |
| Propyl p-hydroxybenzoate | 0.014 g |
| Sterile purified water | suitable amount |
| | Total 100 ml |

An eye drop having the above formulation was prepared by a conventional method.

What is claimed is:

1. A pyridothiazineacetic acid compound of the formula (I)

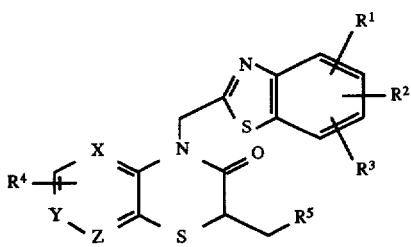

wherein one of X or Y is a nitrogen atom and the other is CH,

Z is CH, $R^1$, $R^2$ and $R^3$ may be the same or different and each is a hydrogen atom, a lower alkyl or a halogen atom, $R^4$ is a hydrogen atom, a lower alkyl or a halogen atom, and $R^5$ is an optionally esterified carboxyl, or a pharmaceutically acceptable salt thereof.

2. The pyridothiazineacetic acid compound of claim 1 wherein, in formula (I), at least one of $R^1$, $R^2$ and $R^3$ is a fluorine atom and $R^5$ is a carboxyl, or a pharmaceutically acceptable salt thereof.

3. The pyridothiazineacetic acid compound of claim 1, which is selected from the group consisting of ethyl 2-[7-chloro-4-(4,5,7-trifluorobenzothiazol-2-yl)-methyl-3-oxo-3,4-dihydro-2H-pyrido[3,2-b][1,4]thiazin-2-yl]acetate, ethyl 2-[4-(4,5,7-trifluorobenzothiazol-2-yl)-methyl-3-oxo-3,4-dihydro-2H-pyrido[3,4-b][1,4]thiazin-2-yl] acetate and 2-[4-(4,5,7-trifluorobenzothiazol-2-yl)methyl-3-oxo-3,4-dihydro-2H-pyrido[3,4-b][1,4]thiazin-2-yl]acetic acid, or a pharmaceutically acceptable salt thereof.

4. A method for producing the pyridothiazineacetic acid compound of claim 1, or a pharmaceutically acceptable salt thereof, comprising (a) reacting a compound of formula (II)

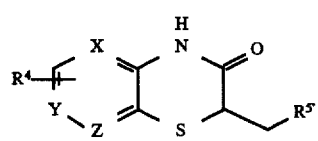

wherein $R^4$, X, Y and Z are as defined above and $R^{5'}$ is an esterified carboxyl, or a salt thereof, with a compound of formula (III)

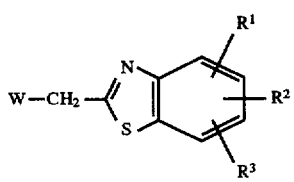

wherein $R^1$, $R^2$ and $R^3$ are as defined above and W is a halogen atom or —$OSO_2R^6$, wherein $R^6$ is lower alkyl, trifluoromethyl or substituted or unsubstituted phenyl, or (b) reacting a compound of formula (IV)

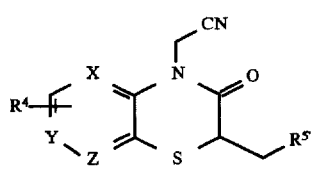

wherein $R^4$, $R^{5'}$, X, Y and Z are as defined above, or an acid addition salt thereof, with a compound of formula (V)

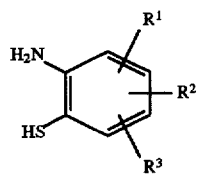

wherein $R^1$, $R^2$ and $R^3$ are as defined above, or an acid addition salt thereof, followed by hydrolysis of the compound obtained in (a) or (b) above, where necessary.

5. A pharmaceutical composition comprising a pharmaceutically effective amount of the pyridothiazineacetic acid compound of any one of claim 1, 2 or 3, or a pharmaceutically acceptable salt thereof, and a pharmaceutically acceptable carrier.

6. A method for inhibiting aldose reductase, comprising administering the pyridothiazineacetic acid compound of claim 1 or a pharmaceutically acceptable salt thereof in an amount effective for inhibiting aldose reductase.

7. A method for preventing and treating the complications of diabetes, comprising administering an effective amount of the pyridothiazineacetic acid compound of claim 1 or a pharmaceutically acceptable salt thereof.

* * * * *

UNITED STATES PATENT AND TRADEMARK OFFICE
CERTIFICATE OF CORRECTION

PATENT NO.   : 5,677,300
DATED        : October 14, 1997
INVENTOR(S)  : Hiroshi, HOSONO, Tomoji, AOTSUKA, Yoshiyuki NAKAMURA, Tetsuo MATSUI and Hiromichi ISHIKAWA It is certified that error appears in the above-identified patent and that said Letters Patent is hereby corrected as shown below:

ON THE TITLE PAGE:

In item [73] change the second Assignee from "Senji Pharmaceutical Co., Ltd." to -- Senju Pharmaceutical Co., Ltd.--.

Signed and Sealed this

Twenty-fourth Day of November, 1998

*Attest:*

BRUCE LEHMAN

*Attesting Officer*   Commissioner of Patents and Trademarks